United States Patent
Chang et al.

(12) 
(10) Patent No.: US 8,334,128 B2
(45) Date of Patent: Dec. 18, 2012

(54) PROBIOTIC SPORE-FORMING LACTIC ACID BACTERIA OF SPOROLACTOBACILLUS VINEAE STRAIN KCTC 11493BP

(75) Inventors: Young-Hyo Chang, Daejeon (KR); Min-Young Jung, Daejeon (KR); In-Soon Park, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 640 days.

(21) Appl. No.: 12/505,338

(22) Filed: Jul. 17, 2009

(65) Prior Publication Data

US 2011/0014166 A1    Jan. 20, 2011

(51) Int. Cl.
*A01N 63/00* (2006.01)
*C12N 1/12* (2006.01)
*C12N 1/20* (2006.01)

(52) U.S. Cl. .................. 435/252.1; 424/93.4; 435/252.9; 435/822; 435/853

(58) Field of Classification Search .................. None
See application file for complete search history.

(56) References Cited

FOREIGN PATENT DOCUMENTS

| KR | 10-0230527 | 8/1999 |
| KR | 10-0858840 | 9/2008 |
| KR | 1020080087568 | 10/2008 |
| WO | 0010582 | 3/2000 |

OTHER PUBLICATIONS

Huang, et al. (2007) Basic characteristics of *Sporolactobacillus inulinus* BCRC 14647 for potential probiotic properties. *Curr. Microbiol.*, 54(5): 396-404.
Chang, et al. (Oct. 2008) *Sporolactobacillus vineae* sp. nov., a spore-forming lactic acid bacterium isolated from vineyard soil. *Int. J. of Systematic and Evolutionary Microbiol.*, 58: 2316-2320.
Sanders, et al. (2003) Sporeformers as Human Probiotics: *Bacillus*, *Sporolactobacillus*, and *Brevibacillus*. Comprehensive Reviews in Food Science and Food Safety, 2:101-110.

*Primary Examiner* — Debbie K Ware
(74) *Attorney, Agent, or Firm* — Greenlee Sullivan P.C.

(57) ABSTRACT

The present invention relates to the novel *Sporolactobacillus vineae* SL153 strain (Accession No: KCTC 11493BP) having probiotic activity, precisely *Sporolactobacillus vineae* SL153 having antimicrobial activity against *Vibrio* genus pathogenic microorganisms and other pathogens. The *Sporolactobacillus vineae* SL153 strain of the present invention has excellent intestinal adherence and growth inhibitory effect on pathogenic microorganisms including *Vibrio* genus microorganisms, so that it can be effectively used as a composition for the prevention and treatment of disease caused by pathogenic microorganisms.

14 Claims, 2 Drawing Sheets

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic construct:  16S rRNA sense primer

<400> SEQUENCE: 1
gagtttgatc ctggctcag                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic construct:  16S rRNA antisens primer

<400> SEQUENCE: 2
ggttaccttg ttacgactt                                                    19
```

-continued

```
<210> SEQ ID NO 3
<211> LENGTH: 1418
<212> TYPE: DNA
<213> ORGANISM: Unknown
<220> FEATURE:
<223> OTHER INFORMATION: Synthettic construct:  Sporolactobacillus sp.
      SL153 16S ribosomal RNA gene, partial sequence
<220> FEATURE:
<221> NAME/KEY: misc_feature
<222> LOCATION: (158)..(158)
<223> OTHER INFORMATION: n is a, c, g, or t

<400> SEQUENCE: 3
tcgagcgcac agaagggagc ttgctcccgg aagtgagcgg cggatgggtg agtaacacgt      60
gggcaacctg cctgaaagtc ggggataact ccgggaaacg ggagctaata ccggataatc     120
gcctgcaccg catggtgcag gtgtgaaaga tggtttcngc catcactttc agatgggccc     180
gcggtgcatt agttagttgg cggggcaacg gcccaccaag accacgatgc atagccgacc     240
tgagagggtg atcggccaca ttgggactga gacacggccc aaactcctac gggaggcagc     300
agtagggaat cttccacaat ggacgaaagt ctgatggagc aacgccgcgt gagcgaagaa     360
ggttttcgga tcgtaaagct ctgttgccgg agaagaacgg acgggagagg aaatgctcct     420
gtcgtgacgg tatccggcca gaaagccacg gctaactacg tgccagcagc cgcggtaata     480
cgtaggtggc aagcgttgtc cggaattatt gggcgtaaag cgcgcgcagg cggtttctta     540
agtctgatgt gaaatcttgc ggctcaaccg caagcggcca ttggaaactg ggaagcttga     600
gtacagaaga ggagagtaga attccacgtg tagcggtgaa atgcgtagag atgtggagga     660
ataccggtgg cgaaggcggc tctctggtct gttactgacg ctgaggtgcg aaagcgtggg     720
gagcaaacag gattagatac cctggtagtc cacgctgtaa acgatgaatg ctaggtgtta     780 gggggtcca acccttagt gctgcagtta acacattaag cattccgcct gggaagtacg     840
accgcaaggt tgaaactcaa aggaattgac ggggcccgc acaagcagtg gagcatgtgg     900
tttaattcga agcaacgcga agaaccttac caggtcttga catccttcga ccgcctgaga     960
gatcaggctt tccccttcgg gggacggagt gacaggtggt gcatggttgt cgtcagctcg    1020
tgtcgtgaga tgttgggtta agtcccgcaa cgagcgcaac ccttgatccc agttgccagc    1080
attcagttgg gcactctggg gtgactgccg gtgacaaacc ggaggaaggt ggggatgacg    1140
tcaaatcatc atgccccta tgatctgggc tacacacgtg ctacaatggg cggtacaaag    1200
ggctgcgaga ccgcgaggtc aagccaatcc cataaagccg ccccagttc ggattgcagg    1260 ctgcaacccg cctgcatgaa gccggaattg ctagtaatcg cggatcagca tgccgcggtg    1320
aatccgttcc cgggccttgt acacaccgcc cgtcacacca cgagagtcgg taacacccga    1380
agtcggtgcg ggaacctta tggacccagc cgccgaag                            1418
```

PROBIOTIC SPORE-FORMING LACTIC ACID BACTERIA OF *SPOROLACTOBACILLUS VINEAE* STRAIN KCTC 11493BP

BACKGROUND OF THE INVENTION

The present invention relates to a novel lactic acid bacteria having probiotics activity.

The genus *Sporolactobacillus* was defined by Kitahara & Suzuki (1963) to accommodate a catalase-negative, spore-forming, homofermentative, lactic acid-producing bacterial species, *Sporolactobacillus inulinus*, within the family Lactobacillaceae. Recently, all members representing Sporolactobacilli were grouped in the family Sporolactobacillaceae (Bergey's Manual of Systematic Bacteriology, Garrity & Holt, 2001). Six species in the genus *Sporolactobacillus* have been reported; they are from rather limited isolation sources. *S. inulinus* was isolated from chicken feed and the other species, *S. kofuensis, S. lactosus, S. laevolacticus, S. nakayamae* and *S. terrae*, were isolated from the rhizosphere or soil around root hairs of a variety of wild plants collected in Japan and South-East Asia, suggesting that *Sporolactobacillus* microorganisms are only isolated from a limited area.

The present inventors completed this invention by confirming that novel *Sporolactobacillus vineae* SL153 (Accession No: KCTC 11493 BP) isolated from soil had high potential for being used as a probiotic strain because it had growth inhibitory effect on *Vibrio* and other various pathogenic microorganisms.

SUMMARY OF THE INVENTION

The present invention provides a novel *Sporolactobacillus vineae* SL153 strain (Accession No: KCTC 11493BP) which inhibits the growth of intestinal pathogenic microorganisms.

The present invention also provides probiotics containing one or more substances selected from the group consisting of the strain, the supernatant thereof and the antimicrobial metabolite recovered from the same as active ingredients.

The present invention further provides a composition for the improvement of intestinal microflora, said composition containing the probiotics as an active ingredient.

The present invention also provides a health food for the improvement of intestinal microflora, said health food containing the said probiotics as an active ingredient.

The present invention also provides a feed additive for the improvement of intestinal microflora, said feed additive containing the said probiotics as an active ingredient.

In addition, the present invention provides a method for producing probiotics containing the step of culturing the said strain.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

The present invention provides a novel *Sporolactobacillus vineae* SL153 strain (Accession No: KCTC 11493BP) which inhibits the growth of intestinal pathogenic microorganisms.

Figure 1:
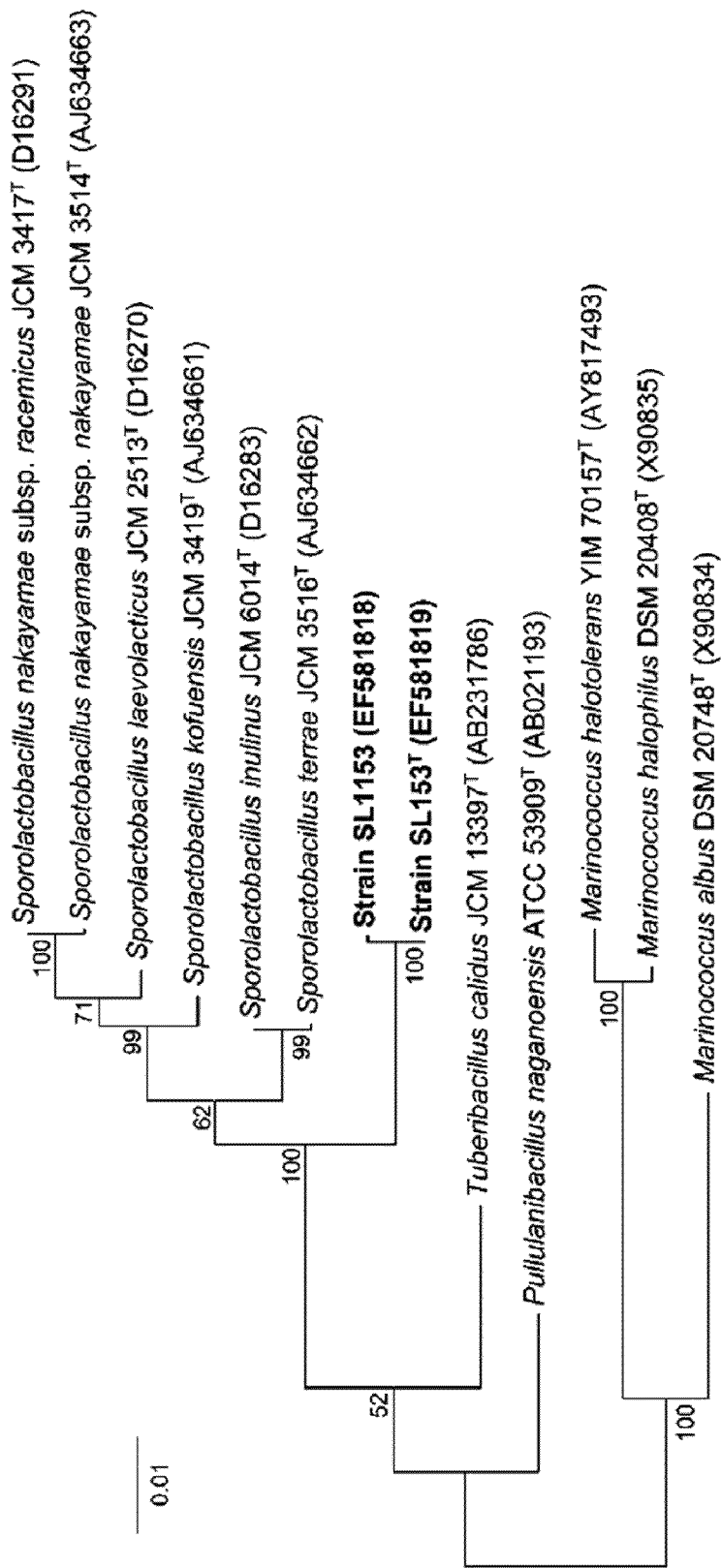
FIG. 1 is a phylogenetic tree based on 16S rRNA sequence of the novel strain (*Sporolactobacillus vineae* SL153; KCTC 11493BP) of the present invention.

In a preferred embodiment of the present invention, the present inventors isolated a lactic acid bacterium characterized as catalase negative and lactic acid and spore forming and named the same as *Sporolactobacillus vineae* SL153 (see FIG. 1).

The present inventors have deposited on Mar. 30, 2009, a sample of *Sporolactobacillus vineae* SL153 designated as "*Sporolactobacillus vineae* SL153" with the Korean Collection for Type Cultures (KCTC) of the Korean Research Institute of Bioscience and Biotechnology (KRIBB) International Depository Authority, at #52 Oun-dong, Yusong-ku, Taejon 305-333, Republic of Korea, in compliance with the Budapest Treaty on the International Recognition of the Deposit of Microorganisms for the Purpose of Patent Procedure as Deposit Accession Number KCTC 11493BP.

The present inventors hereby assure the United States Patent and Trademark Office and the public that (a) all restrictions on the availability to the public of the deposited material described above will be irrevocably removed upon issuance of a United States patent of which any of such deposited material is the subject;

(b) the deposited material will be maintained for a period of at least five years after the most recent request for the furnishing of a sample of any of the deposited material was received by the KCTC and, in any case, for a period of at least 30 years after the date of deposit or for the effective life of such patent, whichever is longer;

(c) should any of the deposits become non-viable or mutated, or otherwise incapable of being furnished by the depository upon request due to the condition of the deposit, it will be replaced by Applicants; and (d) access to the cultures will be available to the Commissioner during the pendency of the patent application or to one determined by the Commissioner to be entitled to such cultures under 37 C.F.R. §1.14 and 35 U.S.C. §122.

The strain has 16S rRNA sequence represented by SEQ. ID. NO: 3.

The intestinal pathogenic microorganism herein can be selected from the group consisting of *Vibrio cholerae, Vibrio alginolyticus, Vibrio fluvialis, Vibrio parahaemolyticus, Aeromonas bivalvium* and *Listonella anguillarum*.

The present invention also provides probiotics containing one or more substances selected from the group consisting of the strain, the supernatant thereof and the antimicrobial metabolite recovered from the same as active ingredients.

In a preferred embodiment of the present invention, the said strain was confirmed to have bile-resistance (see Table 3), growth inhibitory effect on *Vibrio, Aeromonas* and *Listonella* (see Table 4) and excellent intestinal adherence (see FIG. 2), indicating that the strain can be effectively used as a probiotic.

The present invention further provides a composition for the improvement of intestinal microflora, said composition containing one or more substances selected from the group consisting of the *Sporolactobacillus vineae* SL153 strain, the supernatant thereof and the antimicrobial metabolite recovered from the same as active ingredients.

In a preferred embodiment of the present invention, the said strain was confirmed to have bile-resistance (see Table 3), growth inhibitory effect on *Vibrio, Aeromonas* and *Listonella* (see Table 4) and excellent intestinal adherence (see FIG. 2), indicating that the strain can be effectively used as a composition for the improvement of intestinal microflora.

The said composition is preferably a pharmaceutical composition and this pharmaceutical composition can be administered orally or parenterally. For parenteral administration, skin external application, intraperitoneal injection, intrarectal injection, hypodermic injection, intravenous injection, intramuscular injection or intrathoracic injection is preferred.

The said composition has a growth inhibitory effect on a pathogenic microorganism selected from the group consisting of *Vibrio cholerae, Vibrio alginolyticus, Vibrio fluvialis, Vibrio parahaemolyticus, Aeromonas bivalvium* and *Listonella anguillarum*. The composition can be used for the prevention and treatment of a disease selected from the group consisting of acute diarrhea, enteritis, gastroenteritis, constipation, gastralgia, abdominal distention, cholera and food poisoning, but not always limited thereto.

The composition of the present invention can additionally include a pharmaceutically acceptable carrier, for example, an excipient, a disintegrating agent, a sweetening agent, a lubricant and a flavor. The disintegrating agent is exemplified by sodium carboxy methyl starch, crospovidone, croscarmellose sodium, alginic acid, calcium carboxymethyl cellulose, sodium carboxymethyl cellulose, chitosan, guar gum, low-substituted hydroxypropyl cellulose, magnesium aluminum silicate, polacrilin potassium, etc. The pharmaceutical composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1-90 weight part to the composition.

Solid formulations for oral administration are powders, granules, tablets, capsules soft capsules and pills. Liquid formulations for oral administrations are suspensions, solutions, emulsions, syrups and aerosols, and the above-mentioned formulations can contain various excipients such as wetting agents, sweeteners, aromatics and preservatives in addition to generally used simple diluents such as water and liquid paraffin. For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The effective dosage of the composition of the present invention can be determined by those in the art according to absorptiveness of the active ingredient, inactivation rate, excretion rate, age, gender, health condition and severity of a disease. In the case of oral administration, the pharmaceutical composition can be administered by 0.0001-100 mg/kg per day for an adult, and more preferably by 0.001-100 mg/kg per day. The administration frequency is once a day or a few times a day. The dosage cannot limit the scope of the present invention by any means.

The present invention also provides a health food for the improvement of intestinal microflora, said health food containing one or more substances selected from the group consisting of the *Sporolactobacillus vineae* SL153 strain, the supernatant thereof and the antimicrobial metabolite recovered from the same as active ingredients.

For the preparation of the health food, the strain, the supernatant thereof and the antimicrobial metabolite recovered from the same of the present invention can be added as they are or as mixed with other food components according to the conventional method. The mixing ratio of active ingredients can be regulated according to the purpose of use (prevention, health enhancement or sanitation).

The health food herein is not limited. For example, the strain, the supernatant thereof and the antimicrobial metabolite recovered from the same can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in a wide sense, almost every food applicable in the production of health food can be included.

The health food of the present invention can additionally include various flavors or natural carbohydrates, etc, like a conventional health food. The natural carbohydrates above can be one of monosaccharides such as glucose and fructose, disaccharides such as maltose and sucrose, polysaccharides such as dextrin and cyclodextrin, and glucose alcohols such as xylitol, sorbitol and erythritol. Besides, natural sweetening agents such as thaumatin and *stevia* extract, and synthetic sweetening agents such as saccharin and aspartame can be included as a sweetening agent. The content of the natural carbohydrate is preferably 0.01-0.04 g and more preferably 0.02-0.03 g in 100 Ml of the health food of the present invention.

In addition to the ingredients mentioned above, the health food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. All the mentioned ingredients can be added singly or together. The mixing ratio of those ingredients does not matter in fact, but in general, each can be added by 001-0.1 weight part per 100 weight part of the health food of the present invention.

The said health food has the growth inhibitory effect on a pathogenic microorganism selected from the group consisting of *Vibrio cholerae, Vibrio alginolyticus, Vibrio fluvialis, Vibrio parahaemolyticus, Aeromonas bivalvium* and *Listonella anguillarum*.

The present invention also provides a feed additive for the improvement of intestinal microflora, the feed additive containing one or more substances selected from the group consisting of the *Sporolactobacillus vineae* SL153 strain, the supernatant thereof and the antimicrobial metabolite recovered from the same as active ingredients.

The feed additive of the present invention can include general feed ingredients known to those in the art, in addition to the strain, the supernatant and the antimicrobial metabolite of the present invention, which are exemplified by grain powder, carbohydrate, vitamin, amino acid, protein, lipid and mineral, etc.

The feed additive of the present invention can additionally include one or more grains and grain byproducts selected from the group consisting of rapeseed, cottonseed, soybean, bran, rice bran, defatted rice bran, barley bran, corn bran, malt sprouts, soybean hull, potato starch, sweet potato starch, corn starch, coffee meal, litter, silkworm excreta, guano, tapioca, soybean cake, cottonseed meal, perilla meal, rapeseed meal, linseed meal, sesame meal, corn gluten, wheat gluten, peanut meal, coconut meal, sun flower seed meal, dried distillers grains, corn germ meal, red pepper seed meal, soy sauce cake and brewers grains.

The feed additive of the present invention can also include glucose and a complex carbohydrate such as water soluble/insoluble monosaccharide, disaccharide and polysaccharide. Particularly, carbohydrate usable herein is exemplified by glucose, mannose, fructose, white sugar, maltose, cellobiose, lactose, trehalose, melibiose, raffinose, estrin, salicin, amygdalin, mannitol, sorbitol, sorbose, mentitose, and molasses, sucrose and oligosaccharide as well.

The amino acid addable to the feed additive of the present invention is exemplified by arginine, histidine, isoleucine, leucine, lysine, methionine, phenylalanine, threonine, tryptophan, valine, tyrosine, alanine, aspartic acid, sodium glutamate, glycine, proline, serine, cysteine and their analogues and their salts.

The vitamin addable to the feed additive of the present invention is exemplified by thiamine.HCl, riboflavin, pyridoxine.HCl, niacin, niacin amide, inositol, choline chloride, calcium pantothenate, biotin, folic acid, ascorbic acid, and vitamin A, B, K, D and E. Particularly, vitamin A, vitamin B and vitamin E can be used as anti-oxidative agents.

The fatty acid addable to the feed additive of the present invention can be obtained by hydrolysis of vegetable oil such as soybean oil, rapeseed oil, corn oil, white flower oil, sun flower oil, rice oil, beef steak vegetable oil, evening primrose oil, borage oil and flaxseed oil; fish oil isolated from bonito, mackerel and sardine; and a microorganism-originated oil such as a triglyceride. In addition, a metal salt of such fatty acid such as a calcium salt and magnesium salt obtained from the said fatty acid can also be included.

The feed additive of the present invention can additionally include a small amount of well-known bioceramic materials such as plagioclase, bentonite, and elvan to increase antimicrobial activity.

The feed additive of the present invention can additionally include a drug component well-known to those in the art, in particular the additive containing an artificial chemical drug such as an antibiotic, a probiotic, a sweetening agent, an antiacid, and an antidiarrhoeal drug can also be included in the criteria of the feed additive of the present invention. In addition, the feed additive of the present invention can contain shells as a calcium source, and crab-shell and top-shell as a source of mineral such as Fe, Mn, Cu, Zn and Mb.

The said feed additive has a growth inhibitory effect on a pathogenic microorganism selected from the group consisting of Vibrio cholerae, Vibrio alginolyticus, Vibrio fluvialis, Vibrio parahaemolyticus, Aeromonas bivalvium and Listonella anguillarum.

The disease caused by the said pathogenic microorganism is selected from the group consisting of acute diarrhea, enteritis, gastroenteritis, constipation, gastralgia, abdominal distention, cholera and food poisoning.

In addition, the present invention provides a method for producing probiotics containing the step of culturing the Sporolactobacillus vineae SL153 strain.

The method can additionally include the step of recovering the said probiotics. The recovery of the probiotics can be performed by centrifugation, concentration using microfilter or a method using an absorbent.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Isolation and Identification of Strain

To isolate a strain producing lactic acid, the present inventors collected soil samples from vineyard near Taejon, Korea. The vineyard soil sample was diluted and cultured on GYP (glucose-yeast extract-peptone) medium containing 1% $CaCO_3$ at 30° C. for 48 hours. After incubation, acid-producing bacteria were identified by the appearance of clear zones around colonies, selected and purified by repeated isolation three times. The purified microorganism was loaded in a culture medium supplemented with 20% glycerol, which was stored at −80° C.

Molecular phylogenetic analysis was performed with 16S rRNA gene of the isolated strain. Particularly, the cultured cells were suspended in 100 µl of STES buffer [0.4 M NaCl, 0.2 M Tris-HCl(pH 7.6), 0.01 M EDTA, 1% SDS], to which glass beads were added, followed by lysis using microtube mixer MT-360 (TOMY, USA) for 5 minutes to elute cytoplasm. DNA was purified from the eluent using phenol-ethanol PPT and dried using vacuum dryer (SpeedVac, Eppendorf, Germany). The DNA was then dissolved in sterilized distilled water, which was used as a template for PCR. PCR was performed with the primer set of 27F (SEQ. ID. NO: 1,5'-GAG TTT GAT CCT GGC TCA G-3') and 1492R (SEQ. ID. NO: 2,5'-GGT TAC CTT GTT ACG ACT T-3') as follows; denaturation at 94° C. for 1 minute, annealing at 50° C. for 1 minute, polymerization at 72° C. for 1 minute 50 seconds, 30 cycles from denaturation to polymerization. DNA sequencing and phylogenetic analysis were performed by the method well-known to those in the art (Chang et al., Int. J. Syst. Evol. Microbiol. 52: 377-381, 2002).

Morphological characteristics of the selected strain were investigated. As a result, the strain was confirmed to be a Gram-positive bacillus. 16S rRNA gene sequence (SEQ. ID. NO: 3) of the selected strain was investigated. As a result, the strain was identified as a novel Sporolactobacillus having 95.7% homology with Sporolactobacillus inulinus and 95.5% homology with Sporolactobacillus terrae, and it was named Sporolactobacillus vineae. A phylogenetic tree showing the molecular phylogenetic position of the Sporolactobacillus vineae is shown in FIG. 1. The strain was deposited at Korean Collection for Type Cultures, Korean Research Institute of Bioscience and Biotechnology, #52 Oun-dong, Yusong-ku, Taejon 305-333, Korea, on Mar. 30, 2009 under the name of "Sporolactobacillus vineae SL153" (KCTC 11493BP).

EXAMPLE 2

Physiological and biochemical characteristics of Sporolactobacillus vineae SL153

To investigate biochemical characteristics of the strain isolated in Example 1, the strain was cultured using API 50CH system (BioMerieux, Marcy l'Etolite, France) at 37° C. for 24 and 48 hours, followed by analysis of sugar fermentation pattern (Table 1). Optimum culture temperature and pH and salt-resistance of the strain were investigated by using GYP broth. All experiments were accompanied by those with *Sporolactobacillus inulinus* showing 95.7% homology with 16S rRNA of the strain to compare their physiological and biochemical characteristics (Table 1).

TABLE 1

| Characteristic | SL153 | KCTC5032 |
|---|---|---|
| Catalase | − | − |
| Oxidase | − | − |
| Growth temperature range (° C.) | 25-40 | 25-40 |
| Optimal temperature (° C.) | 37 | 37 |
| growth in 7% NaCl | + | w |
| pH range | 6.0-7.0 | 6.0-7.0 |
| Acid production from: | | |
| Glucose | + | + |
| Fructose | + | + |
| Mannose | + | + |
| Galactose | − | − |
| Sorbose | + | − |
| Mannitol | + | + |
| Sorbitol | + | + |
| α-Methyl-D-glucoside | + | + |
| N-acetyl-glucosamine | + | + |
| Amygdalin | − | − |
| Esculin | − | − |
| Salicin | − | − |
| Cellobiose | − | − |
| Maltose | w | w |
| Melibiose | − | |
| Sucrose | w | + |
| Trehalose | w | + |
| Inulin | − | + |
| Raffinose | − | + |
| Starch | − | − |
| Gentiobiose | − | − |
| D-Turanose | + | + |
| D-Tagatose | − | + |

SL153 EXAMPLE 3

Fatty acid composition of *Sporolactobacillus vineae* SL153

To investigate fatty acid composition of the strain isolated in Example 1, the strain was cultured on GYP medium at 37° C. for 24 hours and then the cells were collected. Fatty acid was extracted from the cells according to the MIDI Sherlock System (MIDI, USA). Composition and content of the fatty acid were identified by Gas Chromatography (model 6890N and 7683 autosampler; Agilent, USA) (Table 2).

TABLE 2

| Fatty acid | Content (%) | |
|---|---|---|
| Fatty acid | SL153 | KCTC5032 |
| C14:0 | t | t |
| iso-C15:0 | 13.28 | 12.57 |
| anteiso-C15:0 | 15.17 | 14.25 |
| iso-C16:0 | 4.68 | 5.92 |
| C16:0 | 5.37 | 4.97 |
| iso-C17:0 | 6.09 | 6.13 |
| anteiso-C17:0 | 53.79 | 55.5 |

EXAMPLE 4

Bile-Resistance of *Sporolactobacillus vineae* SL153

To investigate bile-resistance of the strain isolated in Example 1, the strain or *S. inulinus* was spread onto GYP agar plate added with or without bile acid (porcine bile extract, Sigma, St. Louis, Mo., USA) at the concentration of 0.3, 1, 3 and 5% (w/v), followed by culture at 37° C. for 48 hours. The growth of each strain was measured.

As a result, as shown in Table 3, the growth of both *S. vineae* and *S. inulinus* in the media supplemented with 5% bile acid was not inhibited at all, suggesting that they had strong resistance against bile acid.

TABLE 3

| | Bile salt concentration (%) | | | | |
|---|---|---|---|---|---|
| Strain | 0 | 0.3 | 1 | 3 | 5 |
| *Sporolactobacillus vineae* SL153 | T | T | T | T | T |
| *Sporolactobacillus inulinus* KCTC5032 | T | T | T | T | T |

T; bile-resistance

EXAMPLE 5

Growth Inhibitory Effect on Pathogens

To investigate growth inhibitory effect on pathogenic microorganisms, following experiment was performed with *Sporolactobacillus vineae* SL153 and *Sporolactobacillus inulinus* (reference strain). 10 strains including *Escherichi coli* KCTC 2441, provided from KCTC (Korean Collection for Type Cultures, Korean Research Institute of Bioscience and Biotechnology), were used as pathogenic microorganisms. *Escherichi coli* KCTC 2441, *Staphylococcus aureus* KCTC1621, *Salmonella typhimurium* KCTC 1925, and *Edwardsiella tarda* KCTC12267 were cultured on Tryptic soy agar (Difco, USA) and *Vibrio cholerae* KCTC 2715, *V. alginolyticus* KCTC2928, *V. fluvialis* KCTC2473, *V. parahaemolyticus* KCTC2729, *Aeromonas bivalvium* KCTC22102, and *Listonella anguillarum* KCTC2711 were cultured on marine agar (Difco). Experiments were performed according to the methods well-known to those in the art (Chang et al., *Kor. J. Appl. Microbiol. Biotechnol.* 27 (1), 23-27, 1999). The diameter of the inhibition zone (mm) was measured by using paper disc (8 mm, Yoyo Roshi Kaisha, Japan). Concentration of the strain which had been cultured for 18 hours was adjusted to $10^{6-7}$ CFU/ml, followed by distribution on Mueller-Hinton agar and drying. Sterilized disc was inoculated with 100 μl of supernatant of the isolated strain, followed by culture for 48 hours. Equal amount of MRS medium not-inoculated was used as the negative control, followed by comparison of antimicrobial activity.

As shown in Table 4, *S. vineae* had better inhibitory effect on the growth of *Vibrio cholerae, V. alginolyticus, V. fluvialis, V. parahaemolyticus, Aeromonas bivalvium* and *Listonella anguillarum*, compared with *S. inulinus*.

TABLE 4

| | Inhibition (diameter, mm) | | |
|---|---|---|---|
| Strains | SL153 | KCTC5032 | GYP media |
| *Vibrio cholerae* KCTC2715 | 14 | 5 | — |
| *Vibrio alginolyticus* KCTC2928 | 11 | 6 | — |
| *Vibrio fluvialis* KCTC2473 | 11 | 6 | — |
| *Vibrio parahaemolyticus* KCTC2729 | 11 | 4 | — |
| *Aeromonas bivalvium* KCTC22102 | 9 | 5 | — |
| *Escherichia coli* KCTC2441 | — | — | — |
| *Staphylococcus aureus* KCTC1621 | — | — | — |

TABLE 4-continued

| | Inhibition (diameter, mm) | | |
|---|---|---|---|
| Strains | SL153 | KCTC5032 | GYP media |
| *Salmonella typhimurium* KCTC 1925 | — | 15 | — |
| *Edwardsiella tarda* KCTC12267 | — | — | — |
| *Listonella anguillarum* KCTC2711 | 15 | — | — |

EXAMPLE 6

Intestinal Adherence

To investigate intestinal adherence of the strain selected in Example 1, the present inventors used human colon adenocarcinoma cell line HT-29 (ATCC HT-38). *Sporolactobacillus inulinus* was used as the reference strain for comparison with *Sporolactobacillus vineae* SL153. HT-29 was cultured in RPMI 1640 medium (Gibco BRL, USA) supplemented with 10% (v/v) FBS. *S. vineae* strain well-grown on GYP broth was washed with PBS (phosphate-buffered saline) and transferred in serum-free RPMI 1640. Cultured HT-29 strain was distributed in a 16-well cell culture plate (BD science, USA) and followed by culture until monolayer was formed. The prepared *S. vineae* ($10^9$ CFU/Ml) was added thereto, followed by further culture in a 37° C. 5% $CO_2$ incubator. After 2 hours of culture, *S. vineae* not-attached on HT-29 was washed with PBS and the attached strain was recovered by using 0.1% Triton X-100, followed by culture on GYP agar (Difco, USA) at 37° C. for 72 hours. The population of the strain was counted. Intestinal adherence of *S. inulinus* used as the reference strain was also investigated using HT-29 by the same manner as described above.

Figure 2:
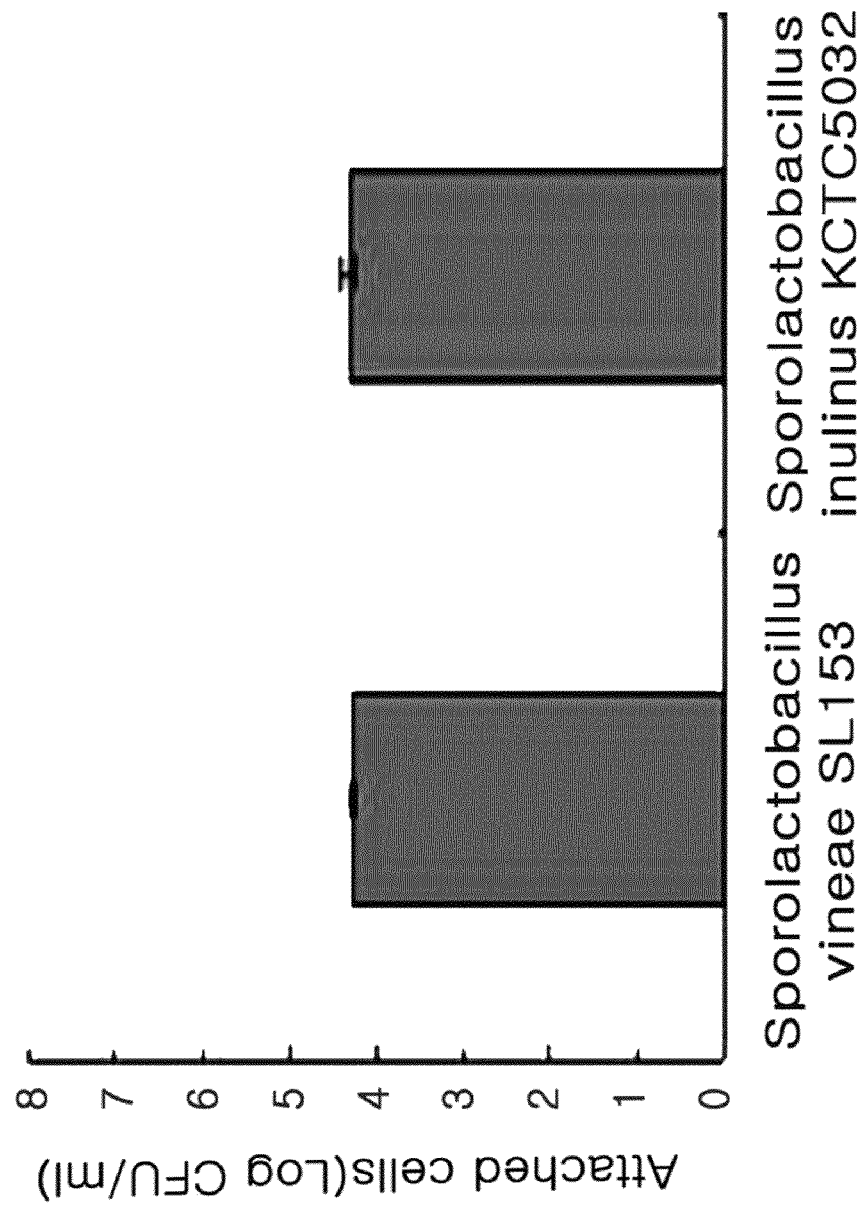
FIG. 2 illustrates the comparison of intestinal adherence between the novel strain (*Sporolactobacillus vineae* SL153; KCTC 11493BP) of the present invention and a reference strain (*Sporolactobacillus inulinus* KCTC 5032).

As a result, compared with *S. inulinus*, the strain of the present invention demonstrated similar intestinal adherence, suggesting that the strain has excellent potential for probiotics (FIG. 2).

EXAMPLE 7

Preparation of Feed Additive

The present inventors prepared a feed additive having the following composition and containing one or more substances selected from the group consisting of *Sporolactobacillus vineae* SL153 strain, the supernatant thereof and the antimicrobial metabolite recovered from the same as active ingredients.

Composition of Feed Additive

| | |
|---|---|
| *Sporolactobacillus vineae* SL153 strain, the supernatant thereof and the antimicrobial metabolite recovered from the same | 0.1~10% weight part |
| Lipase | 0.001~0.01% weight part |
| Calcium phosphate tribasic | 1~20% weight part |
| Vitamin E | 0.01~0.1% weight part |
| Enzyme powder | 1~10% weight part |
| Lactic acid bacteria | 0.1~10% weight part |
| *Bacillus* culture | 0.01~10% weight part |
| Glucose | 20~90% weight part |

EXAMPLE 8

Preparation of Health Food

| Preparation of beverages | |
|---|---|
| Honey | 522 mg |
| Thioctic acid amide | 5 mg |
| Nicotinamide | 10 mg |
| Riboflavin sodium HCl | 3 mg |
| Pyridoxine HCl | 2 mg |
| Inositol | 30 mg |
| Orotic acid | 50 mg |
| *Sporolactobacillus vineae* SL153 strain, the supernatant thereof and the antimicrobial metabolite recovered from the same | 0.48~1.28 mg |
| Water | 200 Ml |

Beverages having the above composition and contents were prepared according to the conventional method.

| Preparation of chewing gum | |
|---|---|
| Gum base | 20% |
| Sugar | 76.36~76.76% |
| *Sporolactobacillus vineae* SL153 strain, the supernatant thereof and the antimicrobial metabolite recovered from the same | 0.24~0.64% |
| Fruit flavor | 1% |
| Water | 2% |

Chewing gum having the above composition and contents was prepared according to the conventional method.

| Preparation of candy | |
|---|---|
| Sugar | 50~60% |
| Corn syrup | 39.26~49.66% |
| *Sporolactobacillus vineae* SL153 strain, the supernatant thereof and the antimicrobial metabolite recovered from the same | 0.24~0.64% |
| Orange flavor | 0.1% |

Candy having the above composition and contents was prepared according to the conventional method.

Preparation of Flour Food 5-10 weight part of the *Sporolactobacillus vineae* SL153 strain, the supernatant thereof and the antimicrobial metabolite recovered from the same of the present invention was added to 100 weight part of flour. Health enhancing food such as bread, cake, cookies, crackers and noodles was prepared with the flour mixture according to the conventional method.

Preparation of Dairy Products 5-10 weight part of the *Sporolactobacillus vineae* SL153 strain, the supernatant thereof and the antimicrobial metabolite recovered from the same of the present invention was added to 100 weight part of milk. Health enhancing dairy products such as butter and ice cream were prepared with the milk mixture according to the conventional method.

EXAMPLE 9

Preparation of Pharmaceutical Formulations

Pharmaceutical formulations containing the *Sporolactobacillus vineae* SL153 strain, the supernatant thereof and the antimicrobial metabolite recovered from the same of the present invention were prepared as follows.

| Preparation of powders | |
| --- | --- |
| *Sporolactobacillus vineae* SL153 strain, the supernatant thereof and the antimicrobial metabolite recovered from the same | 2 g |
| Lactose | 1 g |

Powders were prepared by mixing all the above components, which were filled in airtight packs according to the conventional method for preparing powders.

| Preparation of tablets | |
| --- | --- |
| *Sporolactobacillus vineae* SL153 strain, the supernatant thereof and the antimicrobial metabolite recovered from the same | 100 mg |
| Corn starch | 100 mg |
| Lactose | 100 mg |
| Magnesium stearate | 2 mg |

Tablets were prepared by mixing all the above components by the conventional method for preparing tablets.

| Preparation of capsules | |
| --- | --- |
| *Sporolactobacillus vineae* SL153 strain, the supernatant thereof and the antimicrobial metabolite recovered from the same | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

| Preparation of pills | |
| --- | --- |
| *Sporolactobacillus vineae* SL153 strain, the supernatant thereof and the antimicrobial metabolite recovered from the same | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

| Preparation of granules | |
| --- | --- |
| *Sporolactobacillus vineae* SL153 strain, the supernatant thereof and the antimicrobial metabolite recovered from the same | 150 mg |
| Soybean extract | 50 mg |
| Glucose | 200 mg |
| Starch | 600 mg |

All the above components were mixed, to which 100 mg of 30% ethanol was added. The mixture was dried at 60 and the prepared granules were filled in packs.

INDUSTRIAL APPLICABILITY

The novel strain *Sporolactobacillus vineae* SL153 (Accession No: KCTC 11493BP) of the present invention has not only bile-resistance and excellent intestinal adherence but also growth inhibitory activity against pathogenic microorganisms including *Vibrio* genus microorganisms, so that the strain can be effectively used as probiotics.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A biologically pure microorganism of *Sporolactobacillus vineae* strain KCTC 11493BP which inhibits growth of intestinal pathogenic microorganisms.

2. The *Sporolactobacillus vineae* strain KCTC 11493BP according to claim 1, wherein the strain has the 16S rRNA sequence represented by SEQ ID NO:3.

3. The *Sporolactobacillus vineae* strain KCTC 11493BP according to claim 1, wherein the intestinal pathogenic microorganism is selected from the group consisting of *Vibrio cholerae, V. alginolyticus, V. fluvialis, V. parahaemolyticus, Aeromonas bivalvium* and *Listonella anguillarum*.

4. A probiotic composition comprising the *Sporolactobacillus vineae* strain KCTC 11493BP of claim 1 and a carrier.

5. The probiotic composition according to claim 4, wherein the probiotic composition has growth inhibitory activity against an intestinal pathogenic microorganism selected from the group consisting of *Vibrio cholerae, V. alginolyticus, V. fluvialis, V. parahaemolyticus, Aeromonas bivalvium* and *Listonella anguillarum*.

6. A method for the improvement of intestinal microflora, said method comprising orally or parenterally administering the composition of claim 4 to a subject in need thereof.

7. The method according to claim 6, wherein the composition has growth inhibitory activity against an intestinal pathogenic microorganism selected from the group consisting of *Vibrio cholerae, V. alginolyticus, V. fluvialis, V. para-* haemolyticus, Aeromonas bivalvium and *Listonella anguiflarum*.

8. A health food composition for the improvement of intestinal microflora comprising the *Sporolactobacfflus vineae* strain KCTC 11493BP of claim 1 and health food.

9. The health food composition according to claim 8, wherein the health food is a dairy product.

10. The health food composition according to claim 8, wherein the health food composition has growth inhibitory activity against an intestinal pathogenic microorganism selected from the group consisting of *Vibrio cholerae, V. alginolyticus, V. fluvialis, V. parahaemolyticus, Aeromonas bivalvium* and *Listonella anguillarum*.

11. A feed additive for the improvement of intestinal microflora comprising the *Sporolactobacfflus vineae* strain KCTC 11493BP of claim 1 and a feed ingredient.

12. The feed additive according to claim 11, wherein the feed additive has growth inhibitory activity against an intestinal pathogenic microorganism selected from the group consisting of *Vibrio cholerae, V. alginolyticus, V. fluvialis, V. parahaemolyticus, Aeromonas bivalvium* and *Listonella anguillarum*.

13. A method for producing a probiotic composition comprising the steps of culturing the *Sporolactobacillus vineae* strain KCTC 11493BP of claim 1 in a culture medium, recovering said strain and adding a carrier to form said probiotic composition.

14. The method according to claim 13, wherein the recovering step is performed by one or more methods selected from the group consisting of centrifugation, concentration using microfilter and a method using an absorbent.

* * * * *